United States Patent [19]

Pothmann et al.

[11] Patent Number: 5,361,753
[45] Date of Patent: Nov. 8, 1994

[54] METHOD OF MEASURING AND REGULATING THE PRESSURE IN THE SEALING CUFF OF A TRACHEAL TUBE AND APPARATUS FOR IMPLEMENTING THE METHOD

[75] Inventors: Werner Pothmann; Bastian Steinberg, both of Hamburg; Peter Poock-Haffmans, Wedel; Dirk Harms, Hamburg, all of Germany

[73] Assignee: Deutsche Aerospace AG, Munich, Germany

[21] Appl. No.: 86,889

[22] Filed: Jul. 7, 1993

[30] Foreign Application Priority Data

Jul. 7, 1992 [DE] Germany .......................... 4222220

[51] Int. Cl.⁵ .......................................... A61M 16/00
[52] U.S. Cl. .................. 128/207.15; 128/204.23; 128/748; 128/202.22
[58] Field of Search ............. 128/207.14, 207.15, 128/207.16, 207.17, 200.24, 204.18, 204.23, 202.22, 748, 204.25, 774–782

[56] References Cited

U.S. PATENT DOCUMENTS

| | | | |
|---|---|---|---|
| 4,178,940 | 12/1979 | Au ..................... | 128/207.15 |
| 4,274,423 | 6/1981 | Mizuno et al. ......... | 128/675 |
| 4,278,081 | 7/1981 | Jones ................. | 128/207.15 |
| 4,285,340 | 8/1981 | Gezari et al. ......... | 128/205.24 |
| 4,501,273 | 2/1985 | McGinnis .............. | 128/207.15 |
| 4,502,482 | 3/1985 | DeLuccia et al. ....... | 128/207.15 |
| 4,630,606 | 12/1986 | Weerda et al. ......... | 128/207.14 |
| 4,825,862 | 5/1989 | Sato et al. ........... | 128/207.15 |
| 5,004,472 | 4/1991 | Wallace ............... | 604/194 |
| 5,218,970 | 6/1993 | Turnbull et al. ....... | 128/748 |

FOREIGN PATENT DOCUMENTS

| | | |
|---|---|---|
| 0362824 | 4/1990 | European Pat. Off. . |
| 0366524 | 5/1990 | European Pat. Off. . |
| 9104637 | 7/1991 | Germany .......... 128/207.15 |
| WO91/16097 | 10/1991 | Germany . |
| 1590380 | 8/1976 | United Kingdom ...... 128/207.15 |
| 2060826 | 5/1981 | United Kingdom ...... 128/207.15 |

Primary Examiner—David A. Wiecking
Assistant Examiner—Eric P. Raciti
Attorney, Agent, or Firm—Spencer, Frank & Schneider

[57] ABSTRACT

A processor based method of measuring and regulating the pressure in the inflatable sealing cuff of a tracheal tube introduced into the trachea of a patient, for generating a constant contact pressure of the sealing cuff against the trachea for the purpose of producing gastight respiration for the patient and avoiding the aspiration of fluids from the patient's oral cavity into his breathing passages. The processor receives the actual value of the pressure existing in the sealing cuff as measured by a pressure sensor, detects large and steep increases in pressure in the sealing cuff that deviate from a nominal pressure in the sealing cuff, and interprets the pressure increases as predicting a subsequent widening of the trachea which will result in a decrease of the pressure in the sealing cuff. The processor provisionally increases the pressure in the sealing cuff by adding air for a limited and defined period of time and thereafter regulates the pressure in the sealing cuff gradually toward the original nominal pressure.

13 Claims, 6 Drawing Sheets

METHOD OF MEASURING AND REGULATING THE PRESSURE IN THE SEALING CUFF OF A TRACHEAL TUBE AND APPARATUS FOR IMPLEMENTING THE METHOD

CROSS REFERENCE TO RELATED APPLICATIONS

This application claims the priority of applications Ser. No. P 42 22 220.6 filed Jul. 7, 1992 in Germany, the subject matter of which is incorporated herein by reference.

BACKGROUND OF THE INVENTION

1. Field of the Invention

The present invention relates to a method of measuring and regulating the pressure in an inflatable sealing cuff of a tracheal tube introduced into the trachea of a patient, in particular, for generating a constant contact pressure of the sealing cuff against the trachea for the purpose of producing gas-tight respiration for the patient and avoiding the aspiration of fluids from the patient's oral cavity into his breathing passages, and to an apparatus for implementing the method.

2. Background Information

It is known to employ endotracheal tubes equipped with a cuff that is inflated within the trachea in order to aid the breathing of intensive care patients. The cuff performs two significant functions: it permits gas-tight respiration, and it avoids the aspiration of fluids from the patient's oral cavity into his breathing passages. A fixed cuff pressure of about 20 mbar is usually selected to meet these requirements.

FIG. 1 depicts a cuff arrangement as disclosed in DE-GBM (German Utility Model Patent) 91/04,637 for sealing a cuff 12 on a tube 10 which is inserted into the trachea of a patient. The arrangement includes a compressed air reservoir 14 fed with compressed air from a compressed air source (not shown) by way of a reducing valve 26, a pressure conduit 16 leading from compressed air reservoir 14 to cuff 12, an electrically actuatable air intake valve 18, an electrically actuatable air discharge valve 20, a pressure sensor 22 for measuring the pressure in cuff 12, and a control unit 24. Reducing valve 26 is set to a pressure value that lies clearly above a sealing-pressure of about 20 mbar, but below a pressure which could lead to tearing of the cuff. Control unit 24 measures the actual pressure in cuff 10 with pressure sensor 22 and compares the actual measured pressure with a calculated desired pressure. If the actual measured pressure is determined to be too low, control unit 24 actuates air intake valve 18, so that the pressure in cuff 10 is increased by connection with compressed air reservoir 14. If, however, the actual measured pressure exceeds the desired pressure, air discharge valve 20 is actuated, cuff 12 is thereby connected with the ambient air, and the pressure in the cuff is reduced correspondingly.

However, if there is a great and steep increase in pressure caused, for example, by coughing of the patient, the control unit 24 is not able to respond appropriately.

SUMMARY OF THE INVENTION

According to the present invention, the above described drawbacks and limitations existent in the field are overcome by providing a method of measuring and regulating the pressure in the sealing cuff of a tracheal tube with which a constant contact pressure of the sealing cuff against the patient's trachea is ensured even if there is a great and steep increase in pressure caused, for example, by coughing of the patient. In this way, gas-tight respiration is ensured as is the prevention of the aspiration of fluids from the patient's oral cavity into his breathing passages.

This is accomplished by the present invention in that a control processor recognizes large and steep pressure increases that deviate from a nominal pressure in the sealing cuff and interprets these as predicting a subsequent widening of the trachea which will result in a decrease of the pressure in the sealing cuff. The control processor then provisionally increases the pressure in the sealing cuff by adding air for a limited and defined period of time, whereupon the pressure existing in the sealing cuff is thereafter regulated at a slow speed toward the original nominal pressure.

According to one embodiment, an alarm is initiated if the pressure in the sealing cuff exceeds or falls below alarm pressure thresholds. The alarm pressure thresholds may be programmable. All control and alarm thresholds can be set by way of a patient specific user menu (variable programming), or by way of a standard menu. A standard menu for adults and a standard menu for children may be employed.

An apparatus for implementing the method according to one embodiment of the invention comprises a device for generating compressed air, a compressed air conduit leading to a cuff, an electrically actuatable air intake valve, an electrically actuatable air discharge valve, a pressure sensor measuring the pressure in the cuff, and a control processor, wherein the pressure sensor is disposed in the immediate vicinity of the sealing cuff. According to a further embodiment, the pressure sensor is integrated in the sealing cuff.

In a further embodiment, in addition to the compressed air conduit connecting the sealing cuff with air intake and air discharge valves, a second compressed air conduit is connected to the sealing cuff. In the immediate vicinity of the sealing cuff, the second compressed air conduit is provided with a pressure sensor whose measurement signals are fed to the control processor. The cross sections of the first and second compressed air conduits are selected so that the optimum control behavior results.

These and other objects and aspects of the invention are better understood with reference to the detailed description and accompanying drawings, and it will be understood that changes in the specific structure shown and described may be made within the scope of the claims.

BRIEF DESCRIPTION OF THE DRAWINGS

An exemplary embodiment of the invention is illustrated in the drawing figures, in which.

DETAILED DESCRIPTION OF THE PREFERRED EMBODIMENT

The invention will now be described in more detail by example with reference to the embodiment shown in the Figures. It should be kept in mind that the following described embodiment is only presented by way of example and should not be construed as limiting the inventive concept to any particular physical configuration.

Figure 1:
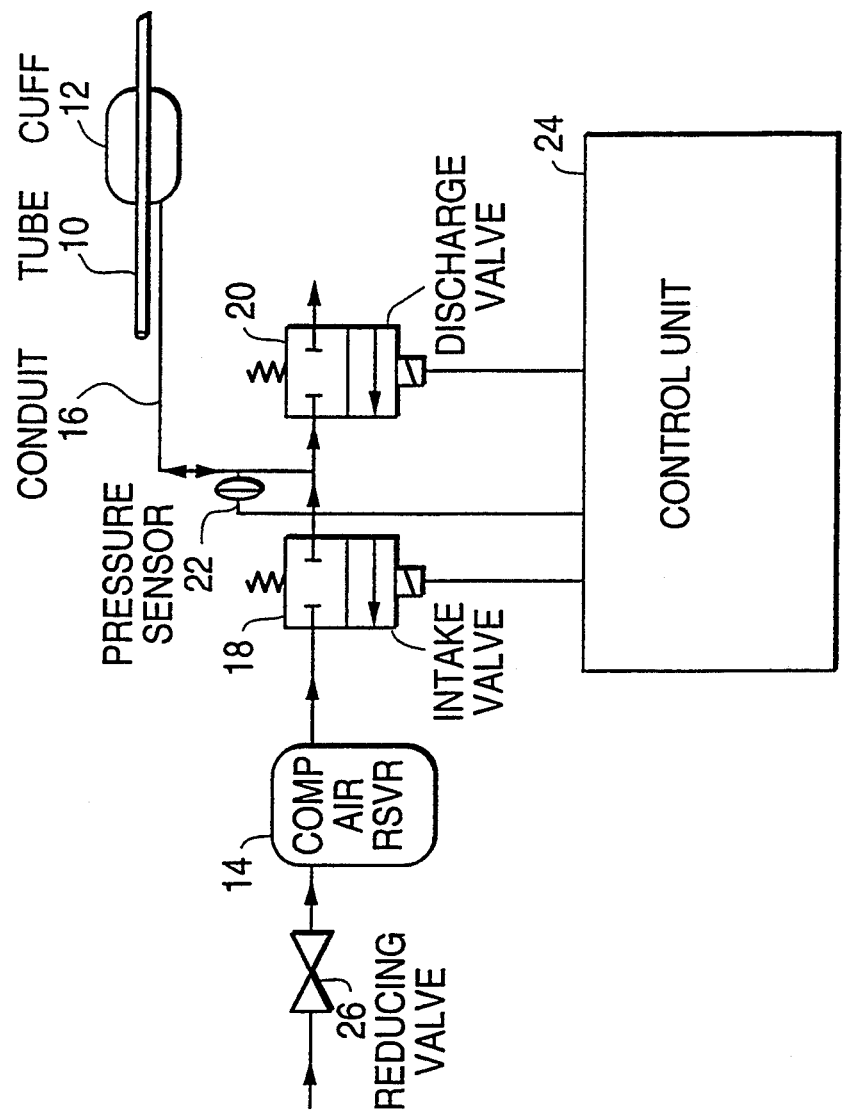
FIG. 1 is a cuff arrangement according to DE-GBM-91/04,637.
Figure 2:
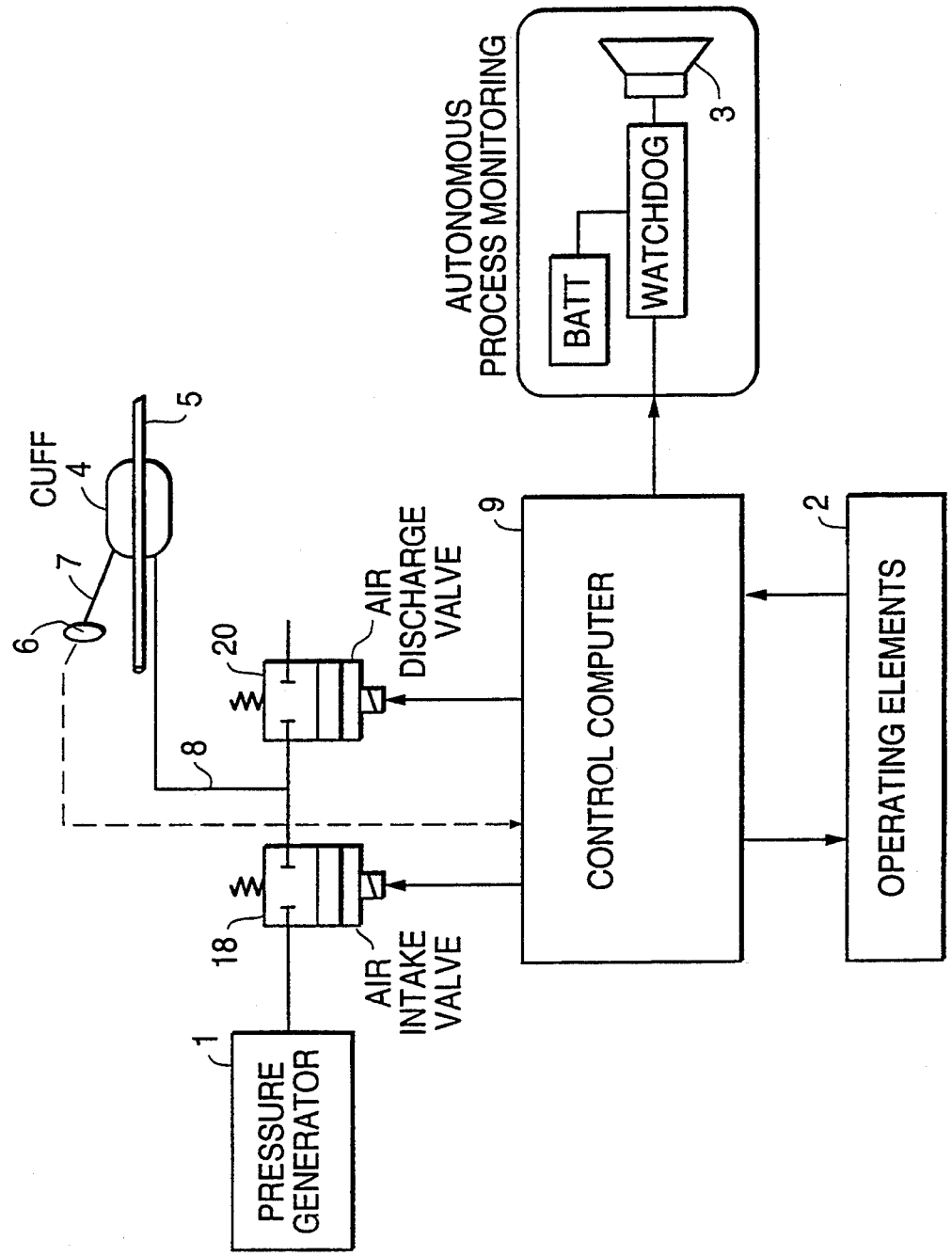
FIG. 2 is a block diagram of an apparatus according to an embodiment of the invention.

The device shown in FIG. 2 differs from the previously described cuff arrangement of FIG. 1, in particular by a simplified configuration of a pressure generator 1, operating elements 2 (keyboard, display screen, etc.) and an autonomous process monitoring unit 3 coupled to a control computer 9 for monitoring its regulating function, and a pressure sensor 6 arranged in the immediate vicinity of the sealing cuff 4 of the tracheal tube 5. As illustrated, pressure sensor 6 is connected to a second compressed air conduit 7, which in turn is connected to sealing cuff 4 in addition to the compressed air conduit 8 connecting sealing cuff 4 with air intake valve 18 and air discharge valve 20. The cross sections of compressed air conduits 7 and 8 are selected in such a way that optimum control behavior results. The cross section of air conduit 7 is chosen to be as large as possible to reach a delayed measurement of pressure. A limit is given through the dimensions of sealing cuff 4. The cross section of air conduit 8 is defined by, the velocity-in which a change of the air volume in sealing cuff 4 is practicable. It is chosen so that a drop in the pressure in sealing cuff 4 can be directly regulated.

Figure 2A:
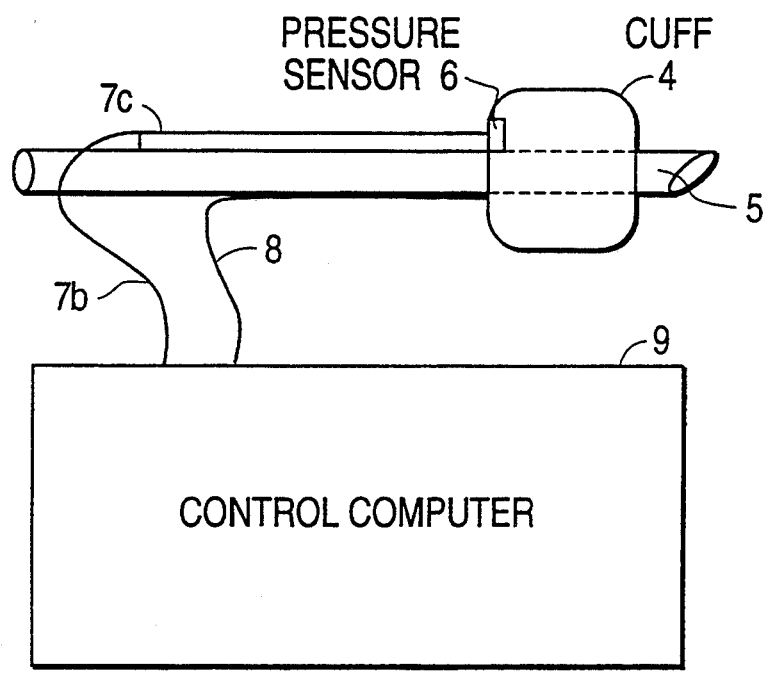
FIGS. 2a, 2b and 2c are further embodiments of the arrangement of sealing cuff, pressure sensor and control unit device.
Figure 2B:
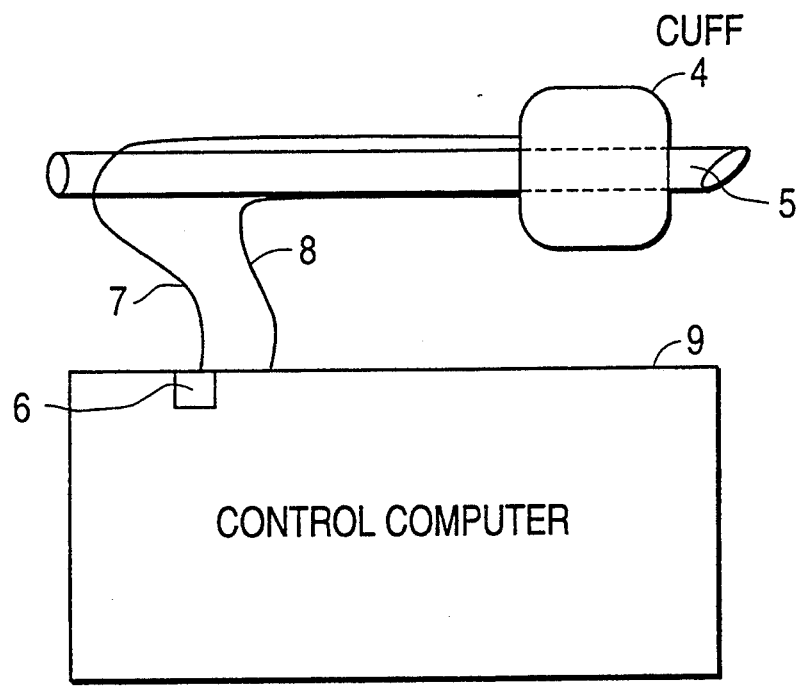
Figure 2C:
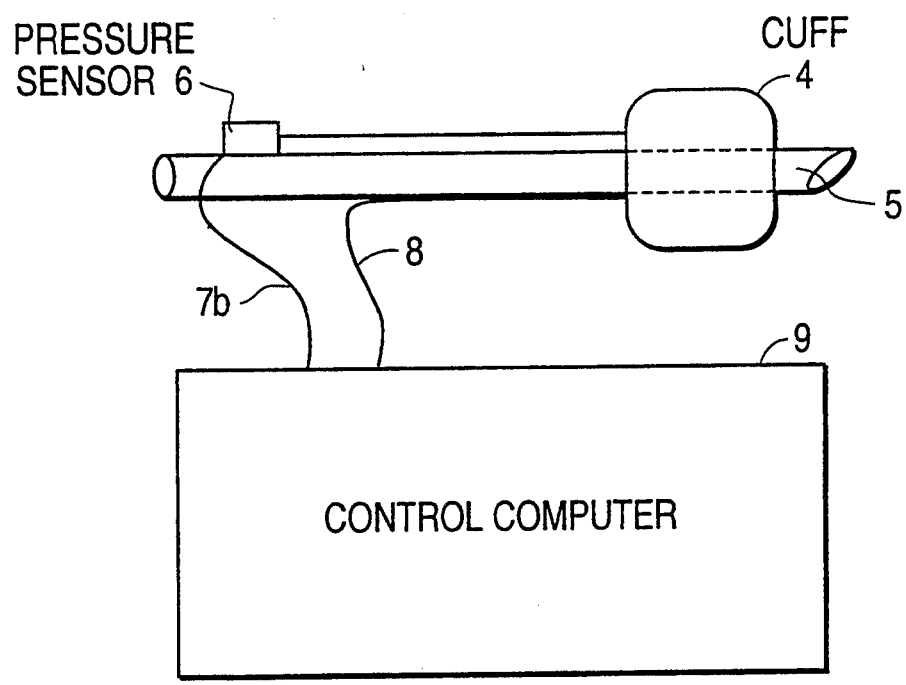

Modifications of the illustrated embodiment within the scope of the invention include, for example, integration of pressure sensor 6 in sealing cuff 4 (FIG. 2a, where the reference pressure for the pressure sensor 6 is lead through the conduit 7c, which is unclosed at its end) or placement of pressure sensor 6 within-compressed air conduit 8 in the immediate vicinity of sealing cuff 4 (FIG. 2c). Advantageously, pressure sensor 6 accurately and quickly reflects the true pressure in cuff 4 due to its immediate proximity to the cuff. Another modification is, for example, the arrangement of the pressure sensor 6 in the control unit device (FIG. 2b). In FIGS. 2, 2a and 2c, the values of the actual measured pressure are transferred to the control unit device with the aid of electrical connection 7b.

Figure 3:
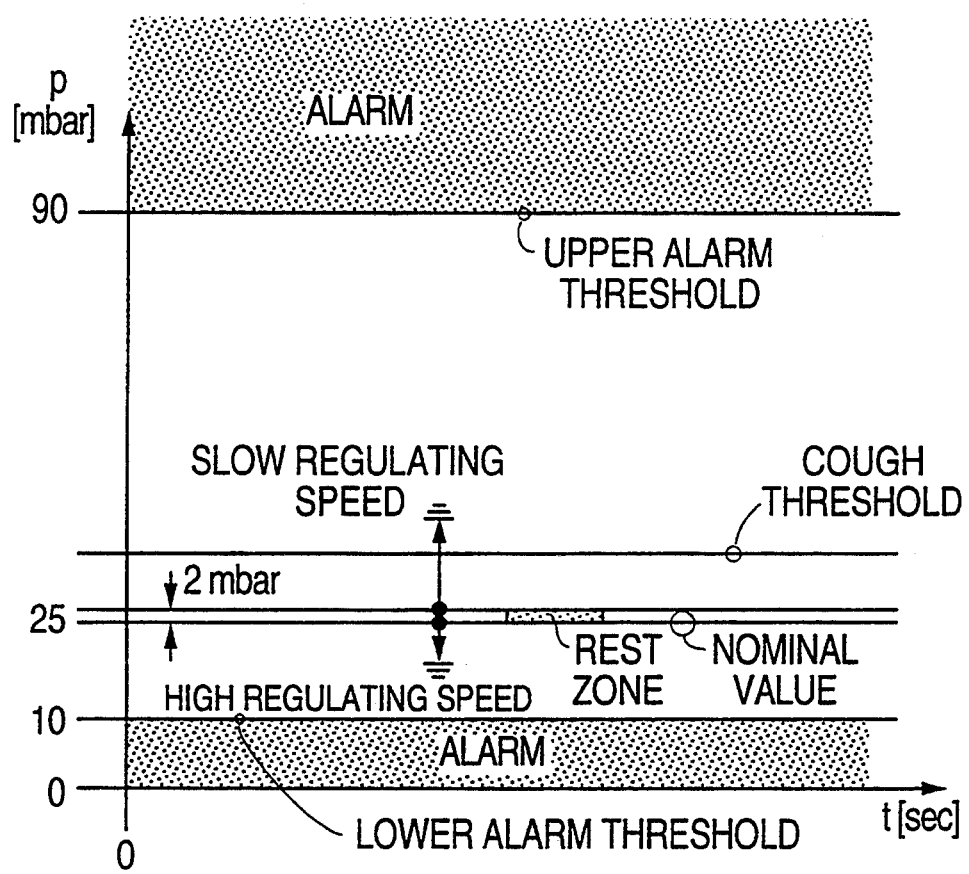
FIG. 3 is a graphic representation of the pressures in the sealing cuff as a function of time.
Figure 4:
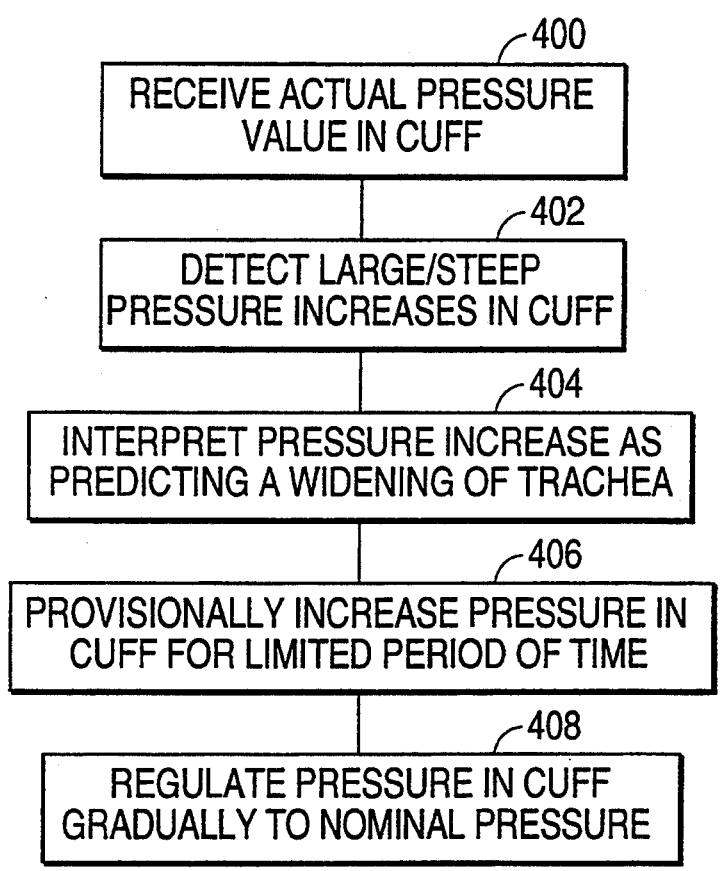
FIG. 4 is a flow chart of a method according to an embodiment of the invention.

With reference to the graphic illustration of FIG. 3, illustrating pressure versus time, and the flow chart of FIG. 4, a method according to the present invention for measuring and regulating the pressure in the sealing cuff 4 of a tracheal tube 5 is now described.

The actual pressure value in the cuff 4 is continuously being sensed with sensor 6 by control computer 9 (step 400). A large and steep pressure increase (step 402) deviating from a nominal (i.e., desired) pressure (value) in sealing cuff 4 caused, for example, by the patient coughing (cough threshold), is sensed by pressure sensor 6 and evaluated (step 404) by the control computer 9 as predicting a subsequent widening of the trachea and, resulting from this widening, a drop in the pressure in sealing cuff 4. The control computer 9 provisionally increases the pressure in sealing cuff 4 (step 406) by causing an intake valve 18 to add air for a limited and defined period of time. Thereafter, control computer 24 regulates the pressure in sealing cuff 4 at a slow speed, i.e., gradually, toward the original nominal pressure (step 408).

With reference to FIG. 3, as indicated by the above statements, the fact that the nominal (desired) pressure value is not reached in sealing cuff 4, is quickly sensed by sensor 6 and results in the immediate and rapid intervention of control computer 9 (high regulating speed). If the momentary pressure (actual value) lies within a defined rest zone, in the illustrated example 2 mbar about the nominal 25 mbar value, control computer 9 does not intervene (dead zone). If the pressure increases to beyond the upper threshold of the rest zone, regulating control computer 9 intervenes at a slow speed in a compensating manner.

If the sealing cuff pressure exceeds or falls below programmable alarm thresholds, in the illustrated example the upper alarm threshold is set at 90 mbar and the lower alarm threshold is set at 10 mbar, an alarm is initiated. Leaks, including micro-leaks, are detected by computing the difference between the air added and discharged and are reported by way of alarm signals.

All control and alarm thresholds are advantageously programmable by way of a keyboard or mouse in conjunction with a user menu displayed on a display device (operating elements). Thus, it is possible to adapt the device to individual requirements of a particular patient. In addition to this variable programming, two predefined programs can advantageously be called up, namely a program for standard use for adults (adult menu) and a program for children (children's menu). These menus would automatically provide nominal adult and child pressure values and thresholds, respectively.

It is understood that various other modifications will be apparent to and can be readily made by those skilled in the art without departing from the scope and spirit of the present invention. Accordingly, it is not intended that the scope of the claims appended hereto be limited to the description set forth above but rather that the claims be construed as encompassing all of the features of patentable novelty which reside in the present invention, including all features which would be treated as equivalents thereof by those skilled in the art to which the invention pertains.

What is claimed is:

1. A processor based method of measuring and regulating pressure in an inflatable sealing cuff of a tracheal tube introduced into the trachea of a patient, for generating a constant contact pressure of the sealing cuff against the trachea for the purpose of producing gas-tight respiration for the patient and avoiding aspiration of fluids from the patient's oral cavity into his breathing passages, the method comprising:

receiving with the processor an actual value of the pressure existing in the sealing cuff as measured by a pressure sensor;

detecting with the processor large and steep increases in pressure in the sealing cuff that deviate from a nominal pressure in the sealing cuff and interpreting the pressure increases as predicting a subsequent widening of the trachea which will result in a decrease of the pressure in the sealing cuff; and provisionally increasing under control of the processor the pressure in the sealing cuff by adding air to the sealing cuff for a limited and defined period of time and thereafter regulating the pressure in the sealing cuff gradually toward the nominal pressure.

2. The method as defined in claim 1, further comprising initiating an alarm if pressure in the sealing cuff exceeds or falls below predetermined alarm pressure thresholds stored in the processor.

3. The method as defined in claim 2, further comprising providing the processor with prestored control and alarm pressure threshold values, wherein the prestored control and alarm pressure threshold values are user changeable.

4. The method as defined in claim 3, further comprising displaying with the processor a patient specific user menu through which control and alarm pressure threshold values may be set by a user and stored by the processor.

5. The method as defined in claim 3, further comprising displaying with the processor at least one standard menu through which control and alarm pressure threshold values may be set by a user and stored by the processor.

6. The method as defined in claim 5, further comprising displaying with the processor one of a standard menu for adults and a standard menu for children.

7. An apparatus for measuring and regulating tracheal sealing cuff pressure, comprising:
  a compressed air pressure generator for providing compressed air;
  a first compressed air conduit leading from the compressed air pressure generator to a tracheal sealing cuff;
  an electrically actuatable air intake valve coupled to the first compressed air conduit and disposed between the compressed air pressure generator and the tracheal sealing cuff;
  an electrically actuatable air discharge valve coupled to the first compressed air conduit and disposed between the tracheal sealing cuff and ambient air;
  a pressure sensor integral with the sealing cuff for measuring the pressure in the tracheal sealing cuff; and
  processor means coupled to the pressure sensor for receiving measurement signals therefrom, for controlling the electrically actuatable air discharge valve and the electrically actuatable air intake valve.

8. A method for measuring and regulating pressure in an inflatable sealing cuff of a tracheal tube introduced into the trachea of a patient, for generating a constant contact pressure of the sealing cuff against the trachea for the purpose of producing gas-tight respiration for the patient and avoiding aspiration of fluids from the patient's oral cavity into his breathing passages which comprises utilizing the apparatus of claim 7.

9. An apparatus for measuring and regulating tracheal sealing cuff pressure, comprising:
  a compressed air pressure generator for providing compressed air;
  a first compressed air conduit leading from the compressed air pressure generator to a tracheal sealing cuff;
  an electrically actuatable air intake valve coupled to the first compressed air conduit and disposed between the compressed air pressure generator and the tracheal sealing cuff;
  an electrically actuatable air discharge valve coupled to the first compressed air conduit and disposed between the tracheal sealing cuff and ambient air;
  a pressure sensor for measuring the pressure in the tracheal sealing cuff;
  processor means coupled to the pressure sensor for receiving measurement signals therefrom, for controlling the electrically actuatable air discharge valve and the electrically actuatable air intake valve; and
  a second compressed air conduit having first and seconds ends, said second compressed air conduit being connected to the sealing cuff at said first end; wherein, the pressure sensor whose measurement signals are fed to the control processor is disposed at the second end of the second compressed air conduit adjacent to the connection with the sealing cuff at said first end.

10. A method for measuring and regulating pressure in an inflatable sealing cuff of a tracheal tube introduced into the trachea of a patient, for generating a constant contact pressure of the sealing cuff against the trachea for the purpose of producing gas-tight respiration for the patient and avoiding aspiration of fluids from the patient's oral cavity into his breathing passages which comprises utilizing the apparatus of claim 9.

11. An apparatus as defined in claim 9, wherein cross sections of the first and second compressed air conduits are configured for optimum control behavior.

12. An apparatus for measuring and regulating tracheal sealing cuff pressure, comprising:
  a compressed air pressure generator for providing compressed air;
  a first compressed air conduit leading from the compressed air pressure generator to a tracheal sealing cuff;
  an electrically actuatable air intake valve coupled to the first compressed air conduit and disposed between the compressed air pressure generator and the tracheal sealing cuff;
  an electrically actuatable air discharge valve coupled to the first compressed air conduit and disposed between the tracheal sealing cuff and ambient air;
  a pressure sensor, disposed in the immediate vicinity of the tracheal sealing cuff, for measuring pressure in the tracheal sealing cuff; and
  processor means coupled to the pressure sensor for receiving measurement signals therefrom, for controlling the electrically actuatable air discharge valve and the electrically actuatable air intake valve, wherein the processor means includes:
    means for receiving an actual value of pressure existing in the tracheal sealing cuff as measured by the pressure sensor;
    means for detecting large and steep increases in pressure in the tracheal sealing cuff that deviate from a nominal pressure in the tracheal sealing cuff and for interpreting the pressure increases as predicting a subsequent decrease of pressure in the tracheal sealing cuff; and
    means for provisionally increasing the pressure in the tracheal sealing cuff by adding air to the tracheal sealing cuff with the electrically actuatable air intake valve for a limited and defined period of time, and for thereafter regulating the pressure in the tracheal sealing cuff gradually toward the nominal pressure with the electrically actuatable air discharge valve.

13. A method for measuring and regulating pressure in an inflatable sealing cuff of a tracheal tube introduced into the trachea of a patient, for generating a constant contact pressure of the sealing cuff against the trachea for the purpose of producing gas-tight respiration for the patient and avoiding aspiration of fluids from the patient's oral cavity into his breathing passages which comprises utilizing the apparatus of claim 12.

* * * * *